United States Patent
Denny

(10) Patent No.: US 6,687,676 B1
(45) Date of Patent: Feb. 3, 2004

(54) PRESCRIPTION VERIFICATION SYSTEM

(75) Inventor: Lawrence A. Denny, Moore, OK (US)

(73) Assignee: Nevoca, Com, Inc., Las Vegas, NV (US)

( * ) Notice: Subject to any disclaimer, the term of this patent is extended or adjusted under 35 U.S.C. 154(b) by 0 days.

(21) Appl. No.: 10/158,259

(22) Filed: May 29, 2002

Related U.S. Application Data

(63) Continuation of application No. 09/400,498, filed on Sep. 21, 1999, now abandoned.

(51) Int. Cl.⁷ .............................................. G06F 17/60
(52) U.S. Cl. ............................................. 705/2; 705/26
(58) Field of Search ........................... 705/2, 3, 26, 27; 700/215, 216; 235/375, 380, 385

(56) References Cited

U.S. PATENT DOCUMENTS

| | | | |
|---|---|---|---|
| 4,193,114 A | 3/1980 | Benini | |
| 4,695,954 A | 9/1987 | Rose et al. | |
| 4,766,542 A | 8/1988 | Pilarczyk | |
| 4,847,764 A | 7/1989 | Halvorson | |
| 4,916,611 A | 4/1990 | Doyle, Jr. et al. | |
| 5,065,315 A | 11/1991 | Garcia | |
| 5,208,762 A | 5/1993 | Charhut et al. | |
| 5,628,530 A | 5/1997 | Thornton | 283/67 |
| 5,737,539 A | 4/1998 | Edelson et al. | 283/67 |
| 5,758,095 A | 5/1998 | Albaum et al. | 395/203 |
| 5,832,449 A | 11/1998 | Cunningham | 705/3 |
| 5,845,255 A | 12/1998 | Mayaud | 705/3 |
| 6,014,631 A | 1/2000 | Teagarden | 705/3 |

FOREIGN PATENT DOCUMENTS

WO    WO 95/25423    *    9/1995

OTHER PUBLICATIONS

Forcinio, Hallie, "Reaping the benefits of bar coding: Quick Response comes to healthcare", Automatic I.D. News, p84, Mar. 1995.*

"Automated Identification of Relevant Patient Information in a Physician's Workstation"; by Henri J. Suermont, Ph.D., Paul C. Tang, M.D., Philip C. Strong, M.D., Charles Y. Young, Ph.D., and Jurgen Annevelink, Ph.D; Hewlett Packard Laboratories, Palo Alto, California, Stanford University School of Medicine, Stanford, CA; 0195–4210/92/$5.00 © AMIA, Inc., 1994.

(List continued on next page.)

Primary Examiner—F. J. Bartuska
(74) Attorney, Agent, or Firm—Dunlap, Codding & Rogers, P.C.

(57) ABSTRACT

A prescription verification system for verifying pharmaceutical prescriptions provided by health care providers to patients which can be filled through any one of a variety of patient-selected pharmacies. The system includes a host system capable of selectively receiving, storing, and dispensing prescription information representative of a prescription for a patient. A unique identification code is associated with each prescription such that each prescription is selectively retrievable. The host system is capable of receiving, storing, and dispensing information representative of the fulfillment of the prescription identified by the prescription information and thereafter assigning a confirmation code to the prescription information so as to indicate whether or not be prescription has been filled. The system further includes a plurality of member health care provider systems remotely disposed from the host system and in communication with the host system. Each of the plurality of member health care provider systems being capable of receiving and inputting prescription information representative of the prescription for the patient into the host system. The member health care provider systems also being capable of retrieving such prescription information. The host system further includes a plurality of member pharmacy systems remotely disposed from the host system and in communication with the host system. The member pharmacy systems being capable of inputting prescription information representative of the prescription for the patient into the hosts system and being capable of receiving and inputting a confirmation code indicative of the prescription being filled into the host system upon fulfilling the prescription.

8 Claims, 4 Drawing Sheets

OTHER PUBLICATIONS

"Patient–Centered Computing: Can It Curb Malpractice Risk?", by Edward E. Bartlett, Ph.D., Department of Community and Family Medicine, Georgetown University School of Medicine; 0195/4210/92/$5.00 © AMIA, Inc., 1994.

"AskRx"; Drug Information Software for Microsoft Windows; Camdat Corporation, 359 Northgate Drive, Warrendale, PA 15086, May 1997.

"Pharmacy Systems Review"; "Pharmacy Automation: Bitter Pills? Or Spoonfuls of Sugar?"; healthcare informatics, Jun. 1993.

* cited by examiner

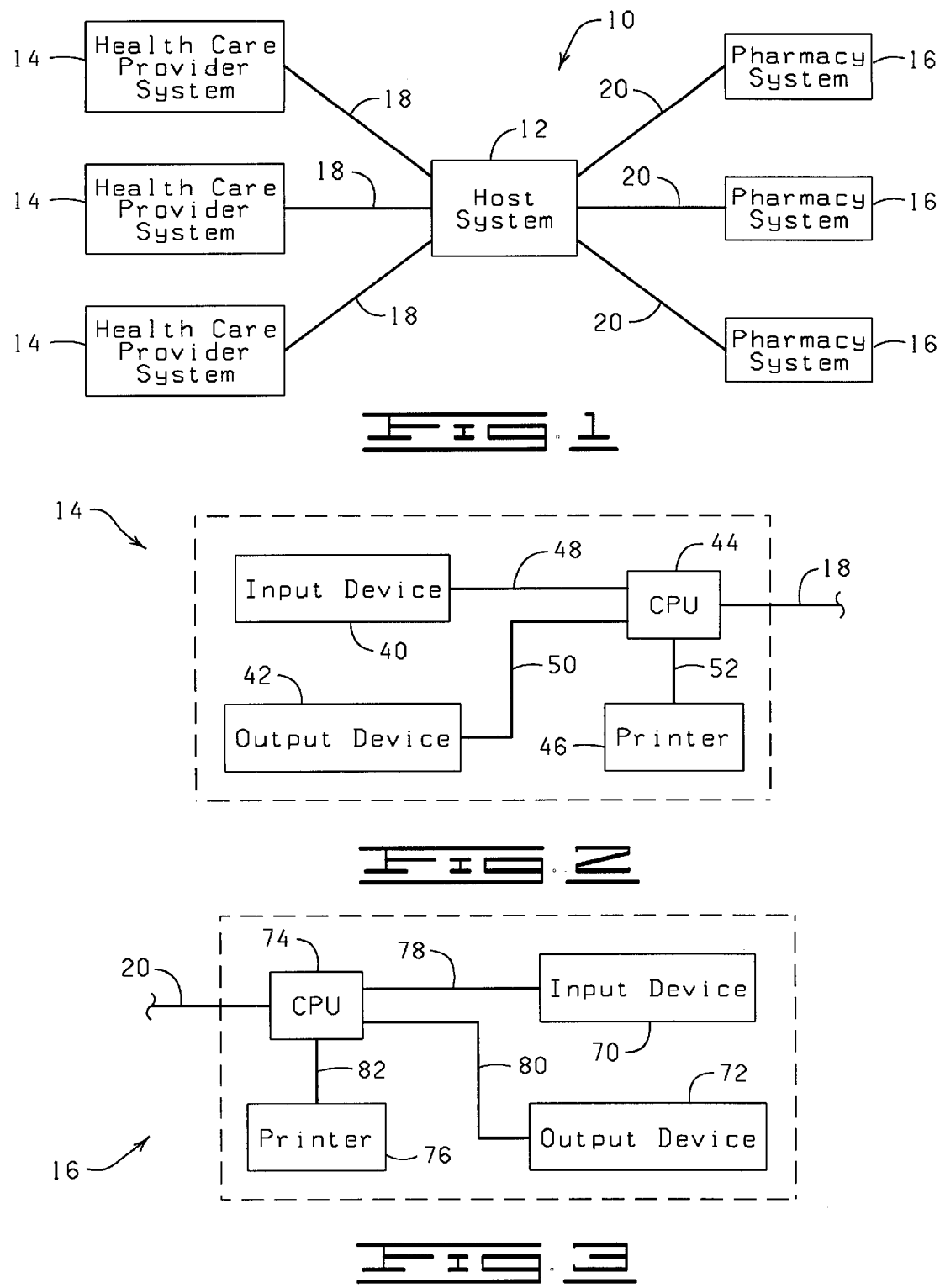

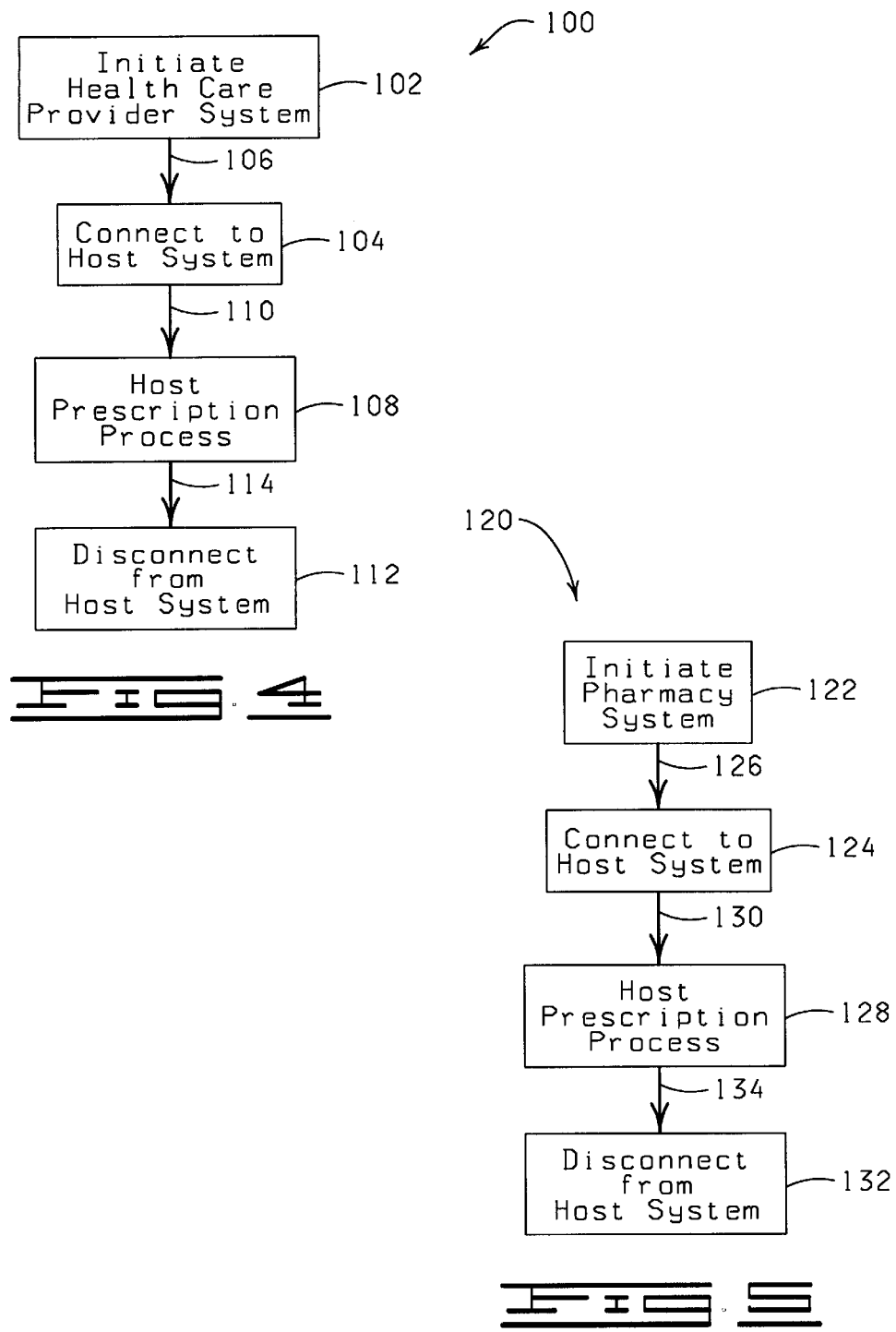

PRESCRIPTION VERIFICATION SYSTEM

CROSS-REFERENCE TO RELATED APPLICATIONS

This application is a continuation of U.S. Ser. No. 09/400,498 filed on Sep. 21, 1999, now abandoned the entire content of which is hereby incorporated by reference.

BACKGROUND OF THE INVENTION

1. Field of the Invention

The present invention relates to a prescription verification system for maintaining information on pharmaceutical prescriptions, and more specifically, but not by way of limitation for verifying the validity and status of prescribed pharmaceuticals.

2. Prior Art

The prescription drug industry consists of several different organizations and professionals. These groups included the health care providers, pharmacies, insurance companies, federal agencies, state agencies, local agencies, and pharmaceutical firms. Each of these groups function virtually autonomous from the others, and each has its own specific interests. This autonomy, coupled with a lack of centralized information, frequently leads to errors in the ordering and filling of drug prescriptions, improper use of prescribed drugs, fraud within the system, and increased costs to each group within the industry.

There are approximately 630,000 prescribers of pharmaceuticals and 76,000 pharmacies in the United States which filled 2.6 billion prescriptions last year. It has been estimated that up to $25 billion per year is attributable to drug fraud and abuse. Additionally, the U.S. General Accounting Office suggests that inappropriate use of prescription drugs exceeds $20 billion per year. Although certain ones of the groups previously mentioned, namely the insurance companies, maintain information relating to their clients, there exists no nationally recognized or easily accessible system for maintaining information on prescription drugs to minimize fraud, abuse, and errors associated with the prescription drug industry.

Furthermore, prescriptions handwritten by physicians are frequently misinterpreted, or completely illegible to the filling pharmacist. Even where such handwritten prescriptions are partially legible, the patient is at great risk of the dosage and special instructions being incorrectly labeled on the final prescription.

Problems also exist with prescribed medications, since patients frequently are unaware of the specific type of medications they are currently taking or simply forget. This presents a serious problem since drug interactions may be dangerous, if not fatal. However, there does not exist a centralized system for a health care provider to determine current prescription medications that a specific patient may be using.

Thus, a need exists for a prescription verification system that is readily accessible to the groups previously mentioned, and more specifically, but not by way of limitation, to the health care provider which prescribes the medications and the pharmacies which fill the prescriptions. It is to a prescription verification system capable of minimizing the fraud abuse and errors associated with prescription drugs that the present invention is directed.

SUMMARY OF THE INVENTION

The present invention relates to a prescription verification system for verifying prescriptions provided by a plurality of health care providers for a plurality of patients which can be filled through any one of a variety of patient-selected pharmacies. Each health care provider is provided with a health care provider system and each pharmacy is provided with a pharmacy system. In operation, a host system receives prescription information including a prescribed drug intended to treat a condition associated with a patient. The prescription information includes a dosage level for the prescribed drug, the drug label contents and any applicable notes to be included on the bottle, a unique health care provider code identifying the health care provider who input the prescription information, and a patient code uniquely identifying the patient.

In response to receiving the prescription information, a unique identification code associated with each prescription information is generated by the host system and the prescription information and the unique identification code associated with the prescription information are stored. Upon request, retrieval information based on the information associated with the prescription information received by the host system is transmitted to a patient-selected pharmacy system. The retrieval information includes the unique health care provider code identifying the health care provider who prescribed the prescription, the patient code uniquely identifying the patient, and the prescription information identifying the prescripted drug, dosage level, the drug label contents, and any applicable notes to be included on the bottle so that the pharmacist at the patient-selected pharmacy is provided with the necessary information to fill the prescription.

In another embodiment the present invention provides a prescription verification system for verifying pharmaceutical prescriptions provided by health care providers to patients which can be filled through any one of a variety of patient-selected pharmacies. The system includes a host system, a plurality of member health care provider systems, and a plurality of member pharmacy systems. The host system is capable of selectively receiving, storing and dispensing prescription information representative of a prescription for a patient and assigning a unique identification code associated with each prescription such that each prescription is selectively retrievable. The host system is also capable of receiving, storing, and dispensing information representative of the fulfillment of the prescription identified by the prescription information and assigning a confirmation code to the prescription information so as to indicate whether or not the prescription has been filled.

The plurality of member health care provider systems is remotely disposed from the host system and in communication with the host system. Each of the plurality of member health care provider systems is capable of receiving and inputting prescription information representative of the prescription for the patient into the host system, and is also capable of retrieving such prescription information. The plurality of member pharmacy systems is remotely disposed from the host system and in communication with the host system. Each of the plurality of member pharmacy systems is capable of inputting prescription information representative of the prescription for the patient into the host system and is also capable of receiving and inputting a confirmation code indicative of the prescription being filled into the host system upon fulfilling the prescription.

The advantages and features of the present invention will become apparent to those skilled in the art when the following description is read in conjunction with the attached drawings and the appended claims.

BRIEF DESCRIPTION OF THE DRAWINGS

FIG. 1 is a diagram depicting a prescription verification system constructed in accordance with the present invention.

FIG. 2 is a schematic, diagrammatic representation, in more detail, of one embodiment of the health care provider system depicted in FIG. 1.

FIG. 3 is a schematic, diagrammatic representation, in more detail, of one embodiment of the pharmacy system depicted in FIG. 1.

FIG. 4. shows the elements and the logic flow diagram for a health care provider system.

FIG. 5. shows the elements and the logic flow diagram for a pharmacy system.

DETAILED DESCRIPTION OF THE PREFERRED EMBODIMENTS

Figure 6:
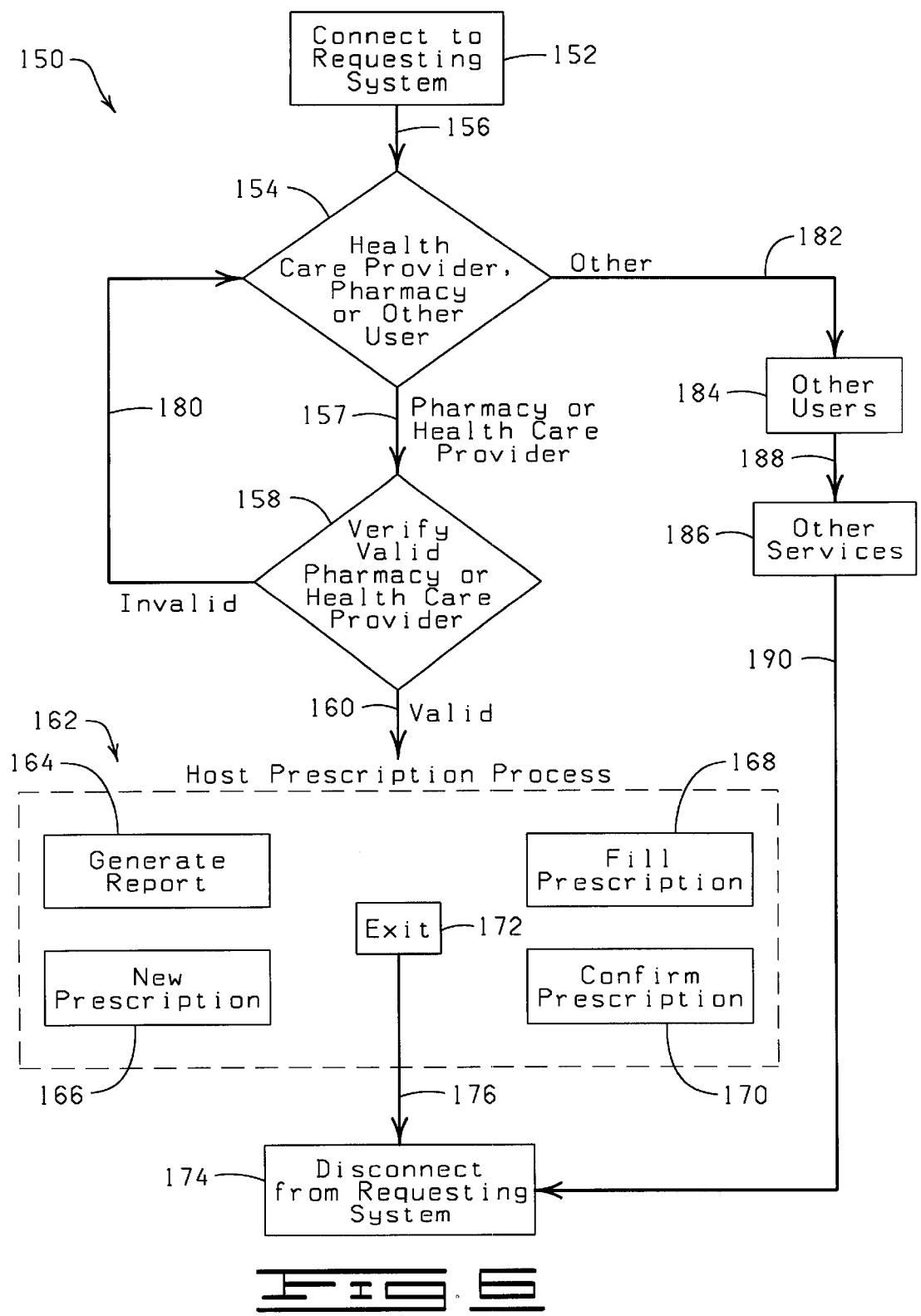
FIG. 6. shows the elements and the logic flow diagram for the host system of the prescription verification system.

Referring now to the drawings and in particular to FIG. 1, shown therein is a prescription verification system 10 which is constructed in accordance with the present invention. The prescription verification system 10 includes a host system 12, a plurality of health care provider systems 14, and a plurality of pharmacy systems 16. The host system 12 can be any system, such as a computer system, which is capable of transmitting and receiving information from a large number of independent and/or non-affiliated systems, such as the health care provider systems 14 and the pharmacy systems 16 where the particular independent and/or non-affiliated systems, such as the health care provider systems 14 and the pharmacy systems 16, transmitting and/or receiving information from the host system 12 are not necessarily chosen by the owner of the host system 12. For example, the host system 12 can be an internet web site capable of transmitting and receiving information onto a public and/or global network, such as the world wide web.

The host system 12 is capable of selectively receiving, storing and dispensing prescription information representative of a prescription for a patient and assigning a unique identification code associated with each prescription such that each prescription is selectively retrievable by the unique identification code, or other information associated with the prescriptions. The host system 12 is also capable of receiving, storing, and dispensing information representative of the fulfillment of the prescription identified by the prescription information and assigning a confirmation code to the prescription information so as to indicate whether or not the prescription has been filled.

The plurality of health care provider systems 14 may be any computer system capable of communicating with the host system 12, such as a personal computer with a web browser, Web TV, or a personal digital assistant. The plurality of health care provider systems 14 are shown in communication with the host system 12 via a communication channel 18. The communication channel 18 may be any communication median capable of transmitting information between the health care provider system 14 and the host system 12, such as an analog or digital telephone line, fiber-optic line, wireless or other electronic communication median for communication between the host system 12, the health care provider system 14 and the pharmacy system 16.

It should be noted that the communication industry is rapidly advancing and there is sure to be communication media developed in the future. It is envisioned that the present invention will also utilize the newly developed communication medians.

The plurality of member health care provider systems 14 are remotely disposed from the host system 12 and in communication with the host system 12. Each of the plurality of member health care provider systems 14 is capable of receiving and inputting prescription information representative of the prescription for the patient into the host system 12, and is also capable of retrieving such prescription information.

The plurality of pharmacy systems 16 may be any computer system capable of communicating with the host system 12, such as a personal computer with a Web browser, Web TV, or a personal digital assistant. The plurality of pharmacy systems 16 are shown in communication with the host system 12 via a communication channel 20. The communication channel 20 may be any communication median capable of transmitting information between the pharmacy system 16 and the host system 12, such as an analog or digital telephone line, fiber-optic line, wireless or other electronic communication median as discussed above with reference to the communication channel 18.

The plurality of member pharmacy systems 16 are remotely disposed from the host system 12 and in communication with the host system 12. Each of the plurality of member pharmacy systems 16 is capable of inputting prescription information representative of the prescription for the patient into the host system 12 and is also capable of receiving and inputting a confirmation code indicative of the prescription being filled into the host system 12 upon fulfilling the prescription.

The prescription verification system 10 is capable of verifying prescriptions provided by the plurality of health care providers, such as physicians, physicians assistants, and administrative individuals associated with the health care provider, for a plurality of patients which can be filled through any one of the variety of patient-selected pharmacies. The health care providers may be affiliated or not affiliated with other health care providers, such as hospitals and hospital affiliated physicians, or unaffiliated clinics and physicians, or combinations thereof. Also, the patient-selected pharmacies may be affiliated or not affiliated with each other, such as Eckerd Drug, Wal-Mart, and\or other independent pharmacies. In other words, each health care provider, such as a doctor, is provided with the health care provider system 14 and each pharmacy is provided with the pharmacy system 16.

In operation, the host system 12 receives prescription information via the communication channel 18 from the health care provider system 14. The prescription information includes a prescribed drug intended to treat a condition associated with a patient. The prescription information also includes a dosage level for the prescribed drug, the drug label contents and any applicable notes to be included on the bottle given to the patient and containing the prescribed drug, a unique health care provider code identifying the health care provider who prescribed the drug, and a patient code uniquely identifying the patient. It should be understood that the term "bottle" as used herein refers to any type of container capable of containing the prescribed drug. The prescription information may also include similar information regarding previous prescriptions which have been prescribed by the health care provider to the patient and whether or not the previous prescriptions have been filled by the pharmacist.

In response thereto, the host system 12 generates a unique identification code associated with each prescription information, and the prescription information is stored by the host system 12, including the unique identification code associated with the prescription information. Upon request, the host system 12 transmits retrieval information based on the information associated with the prescription information received by the host system 12 to a patient-selected pharmacy system 16 via communication channel 20. The retrieval information including the unique health care provider code identifying the health care provider, the patient code uniquely identifying the patient, and the prescription information identifying the prescripted drug and dosage level. Thus it can be seen that the prescription verification system 10 allows pharmacists to verify pharmaceutical prescriptions provided by health care providers to patients which can be filled through any one of a variety of patient-selected pharmacies.

Referring now to FIG. 2, one embodiment of the health care provider system 14 is shown. The health care provider system 14 includes an input device 40, an output device 42, a central processing unit (CPU) 44, a printer 46, and the communication channel 18. The users of the health care provider system 14, such as physicians, physicians assistants, nurses, and administrative personnel associated with the health care provider, input information representative of a prescription for a patient into the health care provider system 14 via the input device 40. The input device 40 can be any device capable of inputting information into the health care provider system 14, such as a keyboard, mouse, scanner, voice-recognition, or other similar devices. The information input into the input device 40 is transmitted along line 48 to the central processing unit 44 for communication to the host system 12 (see FIG. 1) via the communication channel 18.

The health care provider system 14 is capable of receiving prescription information from the host system 12 (see FIG. 1), pursuant to a request from the health care provider system 14, via the communication channel 18. The prescription information received from the host system 12 is processed by the central processing unit 44 and transmitted to the output device 42, via line 50, or the printer 46 via line 52, where the prescription information is capable of being perceived by the user of the health care provider system 14. The output device 42 can be any device capable of outputting information in a format perceivable by an individual, such as a computer monitor. The printer 46 may be any means of outputting prescription information, such as prescription forms printed by a laser printer.

Referring now to FIG. 3, one embodiment of the pharmacy system 16 is shown. The pharmacy system 16 includes an input device 70, an output device 72, a central processing unit (CPU) 74, a printer 76, and the communication channel 20. The users of the pharmacy system 16, such as pharmacists, pharmacists assistants, and administrative personnel associated with the pharmacy, can input information representative or indicative of a prescription to be filled into the pharmacy system 16 via the input device 70 to retrieve the retrieval information discussed above, and, in some instances when authorization is obtained by a physician, to input the prescription information. The input device 70 may be any device capable of inputting information into the pharmacy system 16, such as a keyboard, mouse, scanner, voice-recognition, or other similar devices. The information input into the input device 70 is transmitted along line 78 to the central processing unit 74 for communication to the host system 12 via the communication channel 20.

The pharmacy system 16 is capable of receiving retrieval information, such as information indicative of a prescribed drug intended to treat a condition associated with a patient, and a dosage level for the prescribed drug, the drug label contents and any applicable notes on the bottle, a unique health care provider code identifying the health care provider, and a patient code uniquely identifying the patient from the host system 12, via the communication channel 20. The retrieval information is processed by the central processing unit 74 and transmitted to the output device 72, via line 80, or the printer 76 via line 82, where the retrieval information is capable of being perceived by the user of the pharmacy system 16. The output device 72 can be any device for outputting information in a format perceivable by and individual, such as a computer monitor. The printer 76 can be any means of outputting the retrieval information, such as prescription labels printed by a laser printer.

The pharmacy system 16 is also capable of inputting a confirmation code indicative of the prescription being filled into the host system 12. The confirmation code is input by the user of the pharmacy system 16 into the input device 70 and transmitted to the host system 12 via the central processing unit 74, and via line 78 and communication channel 20 so that the confirmation code is available to any health care provider system 14 or pharmacy system 16 which retrieves the information associated with the prescription. In this way, the problems associated with the repetitive filling of prescriptions is eliminated.

Referring now to FIG. 4, a logic flow diagram of a connection sequence 100 for the health care provider system 14 (see FIG. 1) is shown. The first step 102 is to initiate the health care provider system 14 which may be accomplished, for example where the health care provider system 14 is a personal computer, by powering on the personal computer and launching Internet browsing software, such as Microsoft Internet Explorer. Then, the health care provider system 14 connects to the host system 12 (see FIG. 1) using communication methods well-known in the art or developed in the future as indicated in FIG. 4 by a step 104 and a line 106.

Once the health care provider system 14 connects to the host system 12, the host system 12 processes prescription information received from the health care provider system 14 as indicated in FIG. 4 by a step 108 and a line 110. During the step 108, new prescription information may be input into the host system 12 by the health care provider system 14, and information regarding previously entered prescriptions for the patient prescribed by any health care provider, which are stored in the host system 12, such as previously prescribed and/or filled prescriptions (hereinafter referred to as the patient's "prescription history"), can be received by the health care provider system 14 from the host system 12. This permits the health care provider to take appropriate action based upon the patient's prescription history, or cancel any unfilled prescriptions. After a new prescription has been entered into the host system 12, a printout of the prescription information including the unique code generated by the host system 12 is provided by the printer 46 (FIG. 2) and the printout is presented to the patient, if desired. Thereafter, the health care provider system 14 disconnects from the hosts system 12, such as by terminating the Internet browsing software of the health care provider system 14 as indicated in FIG. 4 by a step 112 and a line 114.

Referring now to FIG. 5, a logic flow diagram of a connection sequence 120 for the pharmacy system 16 (see FIG. 1) is shown. The first step 122 is to initiate the pharmacy system 16 which may be accomplished, for example where the pharmacy system 16 is a personal computer, by powering on the personal computer and launching an Internet browsing software, such as Microsoft Internet Explorer. Thereafter, the pharmacy system 16 connects to the host system 12 (see FIG. 1) using communication methods as discussed above, as indicated in FIG. 4 by a step 124 and a line 126.

Once the pharmacy system 16 is connected to the host system 12, the host system 12 processes prescription information received from the pharmacy system 16 during a step 128 and a line 130. For example, after receiving a prescription, the patient can travel to one of the patient-selected pharmacies and present the printout of the prescription information to a pharmacist. The pharmacist enters the unique code identifying the prescription or other information identifying the patient into the pharmacy system 16 to effect retrieval of the prescription from the host system 12. During the step 128, the patient prescription information is received by the pharmacy system 16 from the host system 12, the prescription is filled by the pharmacist associated with the pharmacy system 16, and a confirmation codes indicative of a prescription being filled is input into the host system 12 by the pharmacy system 16. Thereafter, the pharmacy system 16 disconnects from the host system 12, such as by terminating the Internet browsing software of the pharmacy system 16 as indicated in FIG. 4 by a step 132 and a line 134.

Referring now to FIG. 6, a logic flow diagram 150 for the host system 12 (see FIG. 1) of the prescription verification system 10 is shown. Once the health care provider system 14 or the pharmacy system 16 has initiated the connection sequence 100 and 120, respectively, to connect to the host system 12, the host system 12 proceeds to a first step 152 where the host system 12 connects to such requesting health care provider system 14, pharmacy system 16, or other user, such as an insurance company, federal government organization, or other user. The host system 12 can maintain an introductory or welcome home page screen accessible to all users, such as internet users. Such screen or screens desirably provide information regarding the prescription verification system 10, administrative and advertising information, hypertext links to related Internet web sites and other information beneficial to the use and promotion of the prescription verification system 10. Then, the software running on the host system 12 proceeds to a step 154 along a line 156 to determine the identity of the requesting system.

When the requesting system requests access to the health care provider system 14 or the pharmacy system 16 services on the host system 12, the process branches to a step 158 as indicated by line 157 to verify that the requesting system is a valid health care provider system 14 or pharmacy system 16. The verification screen determines that the requesting system is a valid health care provider system 14 or pharmacy system 16, by using password protection or other security methods known in the art.

The determination that the requesting system is a valid health care provider system 14 or pharmacy system 16 causes the process to branch to a the host prescription process 162 as indicated by a line 160. The host prescription process 162 provides the health care provider system 14 or pharmacy system 16 a variety of options, including a generate report option 164, a new prescription option 166, a fill prescription option 168, a confirm prescription option 170, and an exit option 172 to exit the host system 12. Once the valid health care provider system 14 or pharmacy system 16 completes the host prescription process 162 the next step 174, along a line 176, is for the host system 12 to disconnect from the health care provider system 14 or the pharmacy system 16.

The determination at the verification step 158 that the requesting system is not a valid health care provider system 14 or pharmacy system 16 causes the process to return to step 154 which allows the requesting system to re-select host system 12 services as indicated by a line 180.

Where the requesting system at the step 154 requests other services, such as general information regarding the prescription verification system 10 as previously discussed, the process branches to a step 184 as indicated by a line 182. The other user may select from a variety of other services offered by the host system 12 which causes the process to advance to the next step 186, along a line 188, which provides access to other host system 12 services. The services may include access to non-sensitive prescription information that are of interest to organizations such as insurance companies, federal organizations such as the Drug Enforcement Administration and Medicare, and other organizations desirous of obtaining information regarding pharmaceutical prescriptions maintained in a secure and centralized system.

Additionally these other services may include, as previously discussed, applications and information for becoming a member of the prescription verification system 10 and thus a valid health care provider system 14 or pharmacy system 16, and a discussion of the costs and obligations of such membership. Hyper-links to other organizations of interest as well as general health care related information will be available at the step 186. It will be appreciated that the step 186, as those above, may include a plurality of Internet web pages capable of communicating and receiving the information between the other users and the host system 12. Once the other user completes the other services step 186 the program branches to the step 174, along a line 190, to disconnect from the requesting system.

Figure 7:
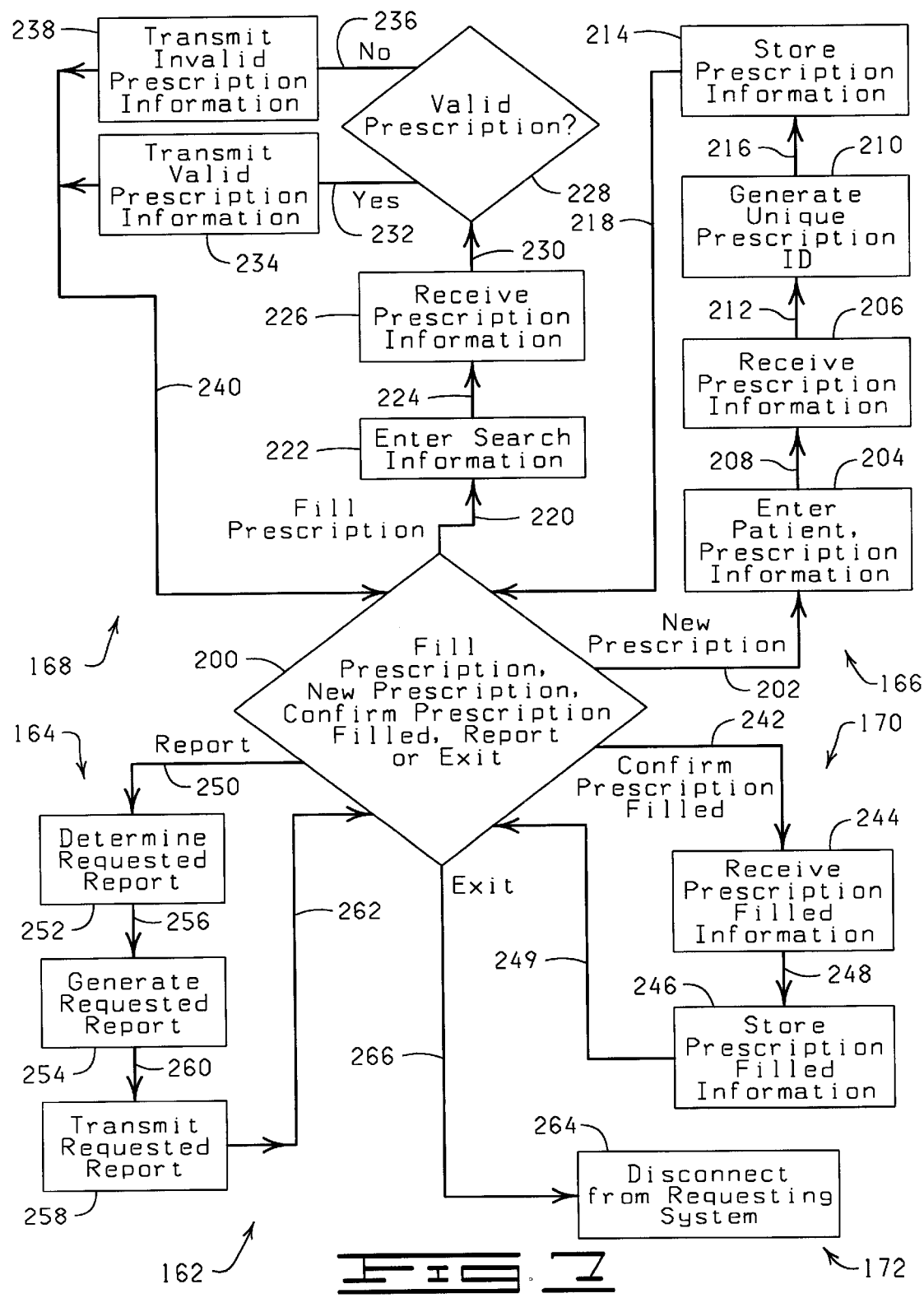
FIG. 7. shows the elements and the logic flow diagram, in more detail, of one embodiment of the host prescription process depicted in FIG. 6.

Referring now to FIG. 7, the host prescription process 162 is shown in more detail. The host prescription process 162 presents the health care provider system 14 (see FIG. 1) and the pharmacy system 16 with a step 200 for selecting a variety of options which may include generate report option 164, new prescription option 166, fill prescription option 168, confirm prescription option 170, and exit option 172 for exiting the host system 12.

In response to the health care provider system 14 or the pharmacy system 16 selecting the new prescription option 166, the process branches to the step 204, as indicated by a line 202, wherein prescription information is entered into the host system 12. Prescription information includes, but is not limited to, patient information such as name, address, telephone and social security number, the prescribed drug, the patient's condition intended to be treated, a dosage level for the prescribed drug, the drug label contents, and any applicable notes which are intended to appear on the label of the bottle, an identifying code uniquely associated with the health care provider, and a patient code uniquely associated with the patient.

It should be appreciated that frequently patients require prescription drugs after normal health care provider hours which are telephoned into a patient-selected pharmacy by the health care provider. In such an event, the prescription verification system 10 allows the pharmacy system 16 in this step 204 to enter the prescription information along with the information about the health care provider which telephoned the prescription to the pharmacy. The inputting of the identifying code uniquely associated with the health care provider is a security measure against fraudulently telephoned prescriptions, while remaining flexible to the realities of modern health care.

At a step 206, along a line 208, the host system 12 receives the prescription information which was previously entered. It will be understood that certain steps, such as data validation, have been omitted since such steps are well known in the art. Thereafter, the process branches along a line 210 to a step 212, where the host system 12 generates a unique prescription identification number. This unique prescription number is associated in the database with the corresponding prescription information. Once the unique prescription identification number is generated, the process branches to a step 214, along a line 216, where the host system 12 stores the prescription information and the unique prescription identification number associated therewith in a database accessible by the host system 12. The process then returns along a line 218 to the options step 200.

Where it is determined that the health care provider system 14 or pharmacy system 16 has selected fill prescription 168, the process branches to a step 222 along a line 220 where search information is entered. The search information which may be used to search the prescription verification system 10 database may include, but is not limited to, the unique prescription identification number, the patient's social security number or name, and the health care provider name or unique code associated therewith. The search information may also include a pharmacy code or a license number associated with the pharmacist filling the prescription, a pharmacy prescription code and unique code associated with the pharmacy system 16. The search information is received by the host system 12 at a step 226, as indicated by a line 224. It should be noted that when the database wherein the prescription information is maintained includes a confirmation code field, i.e. the confirmation code, intended to identify whether not a prescription has been filled, the confirmation code is communicated with the prescription information.

Thereafter, the host system 12 determines whether or not the data received is valid based upon querying the prescription database by a step 228, as indicated by a line 230. Where the information received from the pharmacy system 16 corresponds to prescription information maintained in the host system 12 database, the process branches to a step 234, indicated by a line 232, and transmits a signal to the health care provider 14 or pharmacy system 16 indicating that the prescription information entered is valid. However, where the information received from the pharmacy system 16 does not correspond to prescription information maintained in the host system 12 database, the process branches to a step 238, as indicated by a line 236, and transmits a signal to the health care provider system 14 or pharmacy system 16 indicating that the prescription information entered is invalid.

As a further security measure, upon receiving the prescription information by the pharmacy system 12, the pharmacist may determine, based upon the value of the confirmation code field in the prescription information, that the prescription has been previously filled and therefore may not now be filled. The process then proceeds along a line 240 to the options step 200.

Where it is determined that the health care provider system 14 or the pharmacy system 16 has selected confirm prescription 170, the process branches 242 to the step 244 of receiving prescription filled information. As previously discussed, the prescription information includes a confirmation code which can be an identifier field associated with each prescription indicating whether the prescription has been filled. When a pharmacy system 16 transmits prescription information indicative of a prescription having been filled, the host system 12 modifies the confirmation code so as to indicate that the prescription has been filled. The next step 246, along a line 248, is for the host system 12 to store the prescription information including the confirmation code so as to indicate that the prescription has been filled. Thereafter the process returns to the options step 200, as indicated by a line 249.

Where it is determined that the health care provider system 14 or the pharmacy system 16 has selected generate reports 164, the process branches to a step 252, as indicated by a line 250, to determine the requested report. During this step 252, the health care provider system 14 and pharmacy system 16 are presented with a selection of reports which may be generated by the host system 12 based upon prescription information data maintained in the prescription database by the host system 12. These reports may include prescription data summarized by patient name, social security number, the name of the prescribing health care provider, the physician's Drug Enforcement Agency (DEA) number, and time and transaction based reporting such as daily, monthly prescription reports, and other useful means of organizing and presenting prescription information.

Once the type of report has been selected by the health care provider system 14 or pharmacy system 16 the process branches to a step 254, along a line 256, for the host system 12 to generate the report from the prescription information database. Thereafter the host system 12 transmits, as indicated by a step 258, along a line 260, the requested report from the host system 12 to the requesting health care provider system 14 or pharmacy system 16. Thereafter, the process returns to the options step 200; as indicated by a line 262.

Where the health care provider system 14 or the pharmacy system 16 selects to exit the host system 12 from the option step 200, the system branches to the step 264, as indicated by a line 266, and disconnects from the health care provider system 14 or pharmacy system 16. It will be appreciated that the prescription verification system 10 may include other procedures and utilities, such as software routines located on the host system 12 for maintaining and utilizing an Internet web site and commonly utilized by similarly situated Internet web site systems, such utilities and routines being well known the art and a detailed description is deemed unnecessary.

One example of the operation of the present invention provides a method for verifying prescriptions provided by a plurality of health care providers for a plurality of patients which can be filled through any one of a variety of patient-selected pharmacies with each health care provider being provided with the health care provider system 14 (see FIG. 1) and each pharmacy being provided with the pharmacy system 16 (see FIG. 1). The health care provider diagnoses a patient's condition and determines the appropriate treatment, including prescription medication.

The health care provider initiates the health care provider system at the step 102 (see FIG. 4), and connects to the host system 12 at the step 104 (see FIG. 4). The host system 12 verifies that the health care provider system 14 is a valid health care provider system 14 at step 158 (see FIG. 6). The health care provider system selects, at the step 200, the option to enter a new prescription. The health care provider then inputs via the input device 40 (see FIG. 2) prescription information associated with the medication intended to treat the patient's condition into one of the health care provider systems 14 at the step 204 (see FIG. 7).

The prescription information includes a prescribed drug intended to treat a condition associated with the patient, and a dosage level for the prescribed drug, the drug label contents and any applicable notes on the bottle, a unique health care provider code identifying the health care provider, and a patient code uniquely identifying the patient. The prescription information is then transmitted to the central processing unit 44 (see FIG. 2), via the line 48, and then communicated to the host system 12 (see FIG. 1) along the communication channel 18. The prescription information is then received by the host system 12 at the step 206 (see FIG. 7), and then the host system 12 generates a unique identification code associated with the prescription information and an initial confirmation code indicating whether the prescription has been filled, as indicated by the step 212 (see FIG. 7).

The host system 12 stores the prescription information including the unique identification code associated with the prescription information, and the initial confirmation code indicating whether the prescription contained in the prescription information has been filled at the step 214 (see FIG. 7). The health care provider can then print, via the printer 46 (see FIG. 2), a hard-copy of the prescription to give to the patient.

The patient then selects a pharmacy to fill the prescription and provides the pharmacist associated with the selected pharmacy with the prescription information, such as the hard-copy furnished by the health care provider. The pharmacist then initiates the pharmacy system 16 (see FIG. 1), indicated by the step 122 (see FIG. 5), and connects to the host system 12 at the step 124. Using the input device 70 (see FIG. 2) of the pharmacy system 16, the pharmacist then selects the fill prescription option 168 (see FIG. 7) and inputs the search information associated with the prescription, such as the unique identification code associated with the prescription provided on the printout or hard copy provided by the health care provider system 14 when the prescription was entered into the host system 12, into the host system 12, as indicated by the step 222. The search information is transmitted to the central processing unit 74 (see FIG. 3) on the pharmacy system 16 via the line 78 and then to the host system 12 via the communication channel 20.

The host system 12 receives the search information, at the step 226 (see FIG. 7), and determines whether the search information corresponds with prescription information maintained in the database on the host system 12. The host system 12 may then transmit, at a step 234, to the pharmacy system 16, prescription information including the unique health care provider code identifying the health care provider, the patient code uniquely identifying the patient, the prescription information identifying the prescripted drug and dosage level, the drug label contents and any applicable notes to be included on the bottle given to the patient and containing the prescripted drug, and the confirmation code indicating whether the prescription has been filled. Where no prescription information in the database on the host system corresponds to the search information received from the pharmacy system 16, the host system 12 transmits, at a step 238, a signal to the pharmacy system 16 indicative of the search information being invalid.

If it was determined that the search information corresponds with prescription information maintained in the database on the host system 12, the pharmacist then perceives the prescription information on the pharmacy system 16 on the output device 72 (see FIG. 3) and, for example, reviews the hard copy or printout provided to the pharmacist by the patient for alteration, and/or prints the prescription information using the printer 76. The pharmacist then fills the prescription in accordance with the prescription information when the confirmation code included in the requested prescription information indicates that the prescription has not been filled, or the pharmacist can reject the prescription when the confirmation code included in the requested prescription information indicates that the prescription has been filled.

The pharmacist, using the pharmacy system 16, then selects the option to confirm filling a prescription, as indicated by the step 170 (see FIG. 7). The pharmacist then inputs using the input device 70 (see FIG. 3) of the pharmacy system 16 a confirmation code into the host system 12 via communication channel 20 at the step 244 (see FIG. 7). The confirmation code indicates that the prescription identified by the prescription information has been filled by the patient-selected pharmacist. The host system 12 then stores the confirmation code with the prescription information associated with the prescription into the database on the host system 12. The confirmation code indicating that the prescription has been filled is available to the health care provider systems 14 and the plurality of pharmacy systems 16 so as to indicate that the prescription has been filled or rejected.

From the above description it is clear that the present invention is well adapted to carry out the objects and to attain the advantages mentioned herein as well as those inherent in the invention. While one embodiment of the invention has been described for purposes of this disclosure, it will be understood that numerous changes may be made which will readily suggest themselves to those skilled in the art and which are accomplished within the spirit of the invention disclosed herein and defined in the appended claims.

What is claimed:

1. A method for verifying prescriptions provided by a plurality of health care providers for a plurality of patients which can be filled through any one of a variety of patient-selected pharmacies with each health care provider having a computer system with a web browser and each pharmacy having a computer system with a web browser, the method comprising the steps of:

receiving, via a host system established as a website on the internet, prescription information from a computer system associated with a health care provider, the prescription information including a prescribed drug, and a dosage level for the prescribed drug, the drug label contents and any applicable notes on the bottle, a unique health care provider code identifying the health care provider, and a patient code uniquely identifying the patient;

generating a unique identification code, via the host system, identifying the prescription information;

storing the prescription information including the unique identification code identifying the prescription information;

transmitting prescription information and the unique identification code to the computer associated with the health care provider;

receiving, via the host system, the unique identification code from a computer system associated with a pharmacy; and transmitting, via the host system, retrieval information identified by the unique identification code to the computer system associated with the pharmacy, the retrieval information including the unique health care provider code identifying the health care provider, the patient code uniquely identifying the patient, and the prescription information identifying the prescripted drug and dosage level.

2. The method of claim 1 further comprising the step of receiving, by the host system, a confirmation code to indicate that the prescription identified by the prescription information has been filled by the patient-selected pharmacy.

3. The method of claim 1, wherein in the step of transmitting prescription information and the unique identification code to the computer system associated with the health care provider, a printed prescription is produced by the computer associated with the health care provider having the unique identification code.

4. The method of claim 1, further comprising the step of outputting a report to a computer associated with a user other than a health care provider or a pharmacy.

5. The method of claim 4, wherein the user is associated with a governmental entity.

6. The method of claim 4, wherein the user is associated with an insurance company.

7. The method of claim 4, wherein the report is summarized by the name of the prescribing health care provider.

8. The method of claim 1, further comprising the step of outputting a patient prescription history which includes previous patient prescriptions associated by at least one of a patient code, a health care provider code, and a pharmacy code.

* * * * *